(12) United States Patent
Sablone

(10) Patent No.: US 12,030,682 B2
(45) Date of Patent: Jul. 9, 2024

(54) GRIPPER, AN APPARATUS, AND A METHOD FOR ASSEMBLING KITS OF SANITARY PRODUCTS

(71) Applicant: Fameccanica.Data S.p.A., San Giovanni Teatino (IT)

(72) Inventor: Gabriele Sablone, San Giovanni Teatino (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 0 days.

(21) Appl. No.: 18/080,800

(22) Filed: Dec. 14, 2022

(65) Prior Publication Data

US 2023/0211910 A1  Jul. 6, 2023

(30) Foreign Application Priority Data

Dec. 15, 2021  (EP) .................................. 21214853

(51) Int. Cl.
| | |
|---|---|
| *B65B 35/16* | (2006.01) |
| *A61F 13/551* | (2006.01) |
| *B65B 5/06* | (2006.01) |
| *B65B 35/02* | (2006.01) |
| *B25J 9/00* | (2006.01) |

(52) U.S. Cl.
CPC .......... *B65B 35/16* (2013.01); *A61F 13/5514* (2013.01); *B65B 5/06* (2013.01); *B65B 35/02* (2013.01); *B25J 9/0093* (2013.01)

(58) Field of Classification Search
CPC ......... B65B 35/16; B65B 35/02; B65B 35/36; B65B 5/06; B65B 5/068; B65B 2220/14; B65B 25/145; B65B 59/001; A61F 13/5514; A61F 13/15747; B25J 9/0093; B25J 9/1612; B25J 9/1679; G05B 2219/45048; B65J 15/0253; B65J 15/10
See application file for complete search history.

(56) References Cited

U.S. PATENT DOCUMENTS

| | | | |
|---|---|---|---|
| 5,106,138 A | 4/1992 | Lawson | |
| 8,060,248 B1 * | 11/2011 | Boyer | ..................... B65B 57/20 700/235 |
| 8,777,552 B2 | 7/2014 | Ward et al. | |
| 9,486,927 B1 * | 11/2016 | Morey | ................. B25J 15/0061 |

(Continued)

FOREIGN PATENT DOCUMENTS

| | | |
|---|---|---|
| CN | 209853202 U | 12/2019 |
| CN | 211365104 U | 8/2020 |

(Continued)

OTHER PUBLICATIONS

European Search Report dated Aug. 29, 2022. 13 pages.

*Primary Examiner* — Thomas M Wittenschlaeger
*Assistant Examiner* — Himchan Song
(74) *Attorney, Agent, or Firm* — RMCK Law Group PLC

(57) ABSTRACT

A gripper, an apparatus, and a method for assembling kits of sanitary products in an automated fashion are disclosed. The sanitary products are pre-loaded into containers including a plurality of independent housings for the sanitary products, each of the housings being configured to allow loading of a sanitary product therein and withdrawal of the sanitary product therefrom independently of the other housings, and the kit is assembled in batches on the gripper, and released by the latter into a package.

13 Claims, 10 Drawing Sheets

(56) References Cited

U.S. PATENT DOCUMENTS

| | | | | |
|---|---|---|---|---|
| 11,735,304 B2* | 8/2023 | Chambers | ............... | G07F 9/006 |
| | | | | 53/473 |
| 2001/0019065 A1* | 9/2001 | William | ................. | G07F 11/32 |
| | | | | 221/109 |
| 2006/0259195 A1* | 11/2006 | Eliuk | ................. | B01F 33/8442 |
| | | | | 700/245 |
| 2012/0177473 A1* | 7/2012 | Smith | ................. | G07F 17/0092 |
| | | | | 414/744.3 |
| 2020/0306992 A1* | 10/2020 | Inui | ..................... | B25J 15/0253 |
| 2021/0245970 A1 | 8/2021 | Ackermann et al. | | |

FOREIGN PATENT DOCUMENTS

| | | |
|---|---|---|
| IT | 202000003212 A1 | 8/2021 |
| WO | 2014072951 A1 | 5/2014 |

* cited by examiner

FIG. 1A
FIG. 1B
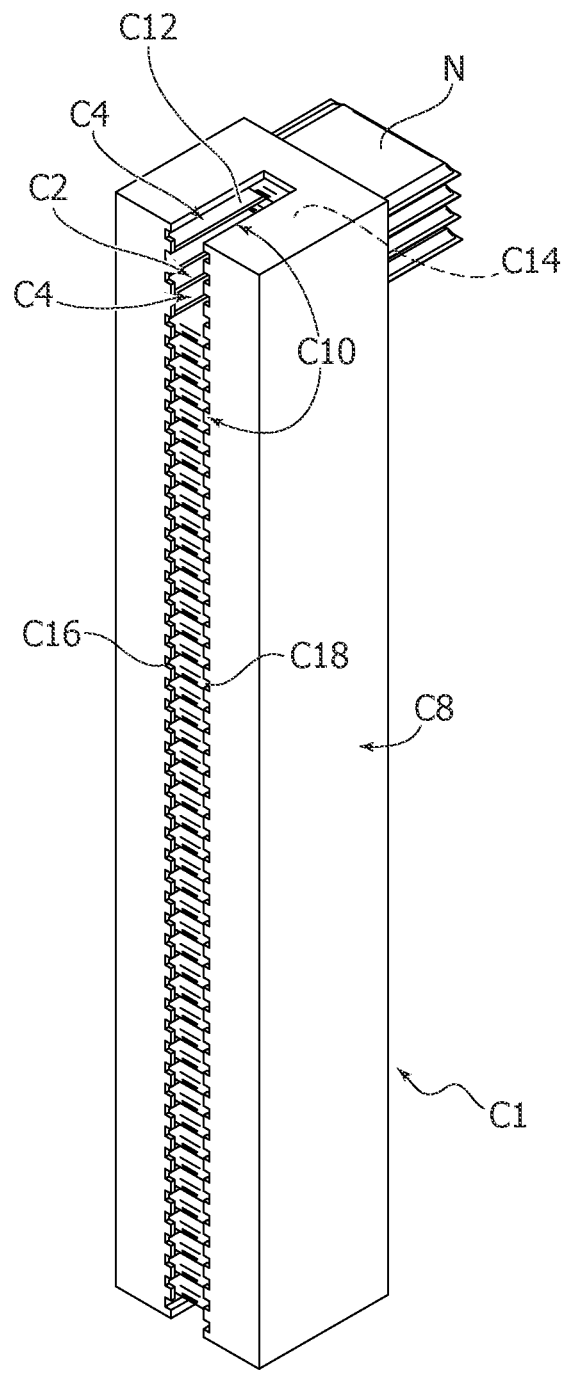
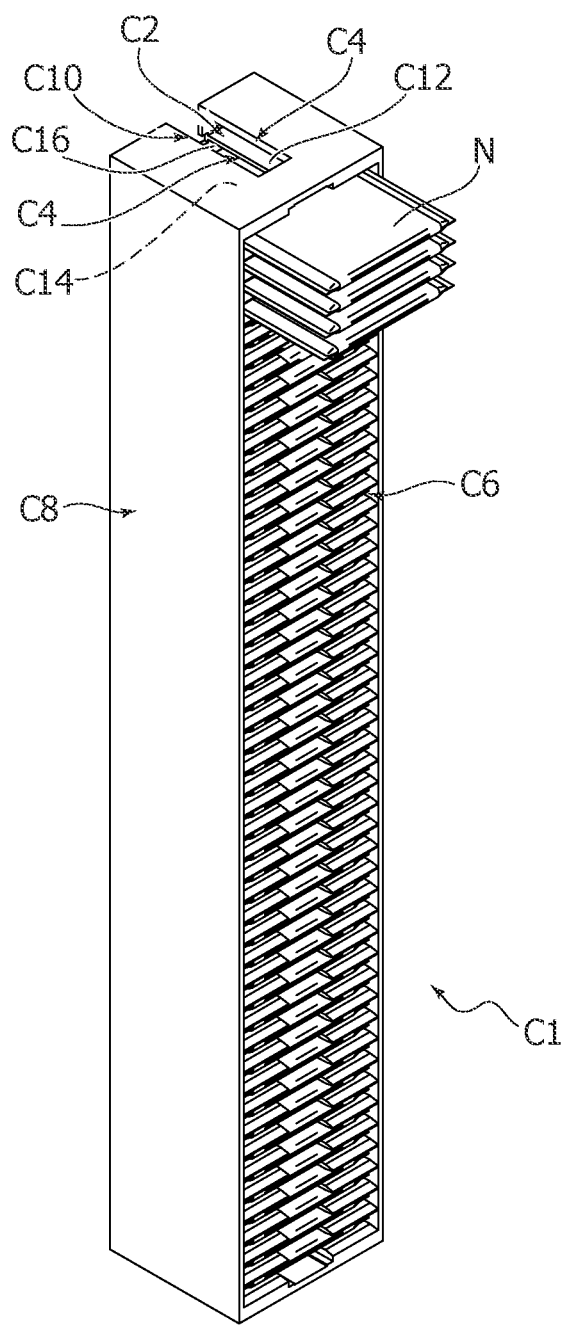

GRIPPER, AN APPARATUS, AND A METHOD FOR ASSEMBLING KITS OF SANITARY PRODUCTS

CROSS-REFERENCE TO RELATED APPLICATION

This application claims priority to European Patent Application No. 21214853.0 filed Dec. 15, 2021. The disclosure of the above application is incorporated herein by reference in its entirety.

FIELD OF THE INVENTION

The present invention relates to the packaging of sanitary products, particularly sanitary napkins.

PRIOR ART

Sanitary napkins are marketed all over the world in single format, single size packages. In other words, all of the sanitary napkins within the package are all identical and all have, accordingly, the same size and the same absorbent features.

The variability of the blood flow during a period calls for the use of different sanitary napkins throughout the period, starting from bigger and/or more absorbent products on the initial days, and transitioning to lighter or less absorbent products towards the final days. In view of the features of the packages of sanitary napkins, customers have no other option than buying multiple packages of different sanitary napkins, and picking the desired sanitary napkin from the corresponding package. This is clearly a drawback as the customer is forced to buy sanitary napkins way in excess of what would be actually needed to face the needs of the period.

An ideal condition would be that of having a mix of sanitary napkins configured to address the needs of different stages of the period all packaged together, so that the customer can buy a single packaged with napkins assembled as a "period kit", rather than a stack comprising one and the same product.

The technical problem underlying this derives from the manufacturing process that outputs the packaged sanitary napkins. Differently sized and/or differently performant sanitary napkins are usually manufactured by different machines operating in separate manufacturing and packaging lines.

The Applicant has already tackled this technical problem in European Patent application no 21201297.5. disclosing a method, an apparatus and a container which make it possible to merge different manufacturing lines together, with the result "period kits", i.e. packages including a full range of sanitary napkins which address the needs of different stages of the period, can be assembled in an automated fashion. Still, technical problems remain especially as far automated packaging efficiency is concerned. Available automated packaging solutions may be affected by sub-optimal packaging rates due to the difficulties in assembling kits of different products, and even packaging operations per se may be affected by technical problems such as jamming of the end effector of the robot that picks and places the sanitary products into the package (usually a box) due to the cramped available space, and/or package tearing or rupturing by the end effector.

OBJECT OF THE INVENTION

The object of the invention is to solve the above-mentioned technical problems. Particularly, the object of the invention is to provide a device, an apparatus and a method for assembling, in an automated fashion, packages for sanitary napkins including a range of differently sized and/or differently performing sanitary napkins altogether making up a period kit which has a higher operation (packaging) rate, and is effective in preventing jams or ruptures at the packaging containers.

SUMMARY OF THE INVENTION

The object of the invention is achieved by a device, an apparatus and a method having the features forming the subject of the claims that follow, which form an integral part of the technical disclosure provided herein in relation to the invention.

BRIEF DESCRIPTION OF THE FIGURES

Further features and advantages of the invention will become apparent from the following description with reference to the annexed drawings, provided purely by way of non limiting example, wherein:

FIGS. 1A and 1B are perspective views from different angles of containers of sanitary products configured for use with the gripper and the apparatus of the invention.

DETAILED DESCRIPTION

Figure 1:
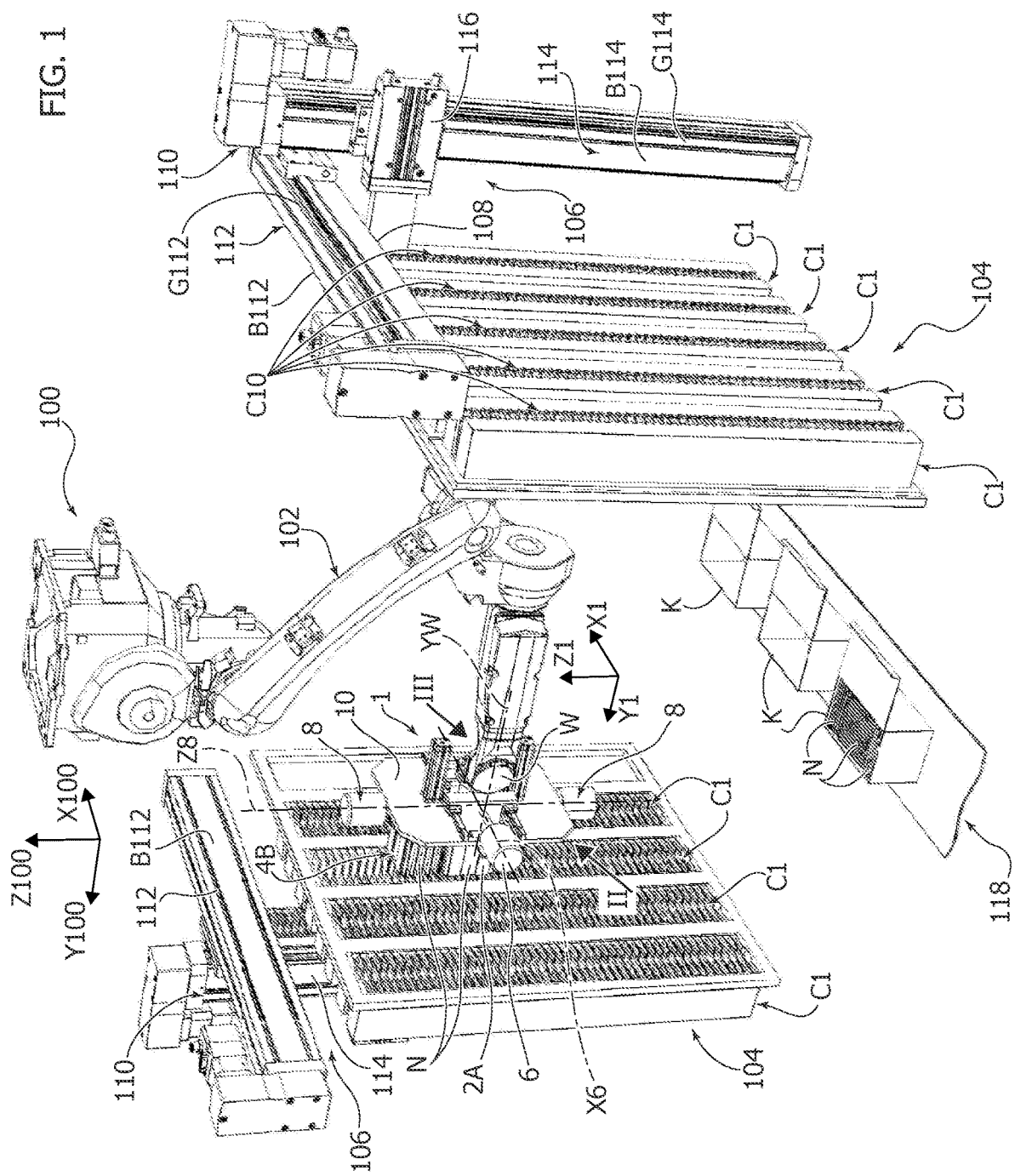
FIG. 1 is a perspective view of an apparatus and a gripper according to the invention.
Figure 2:
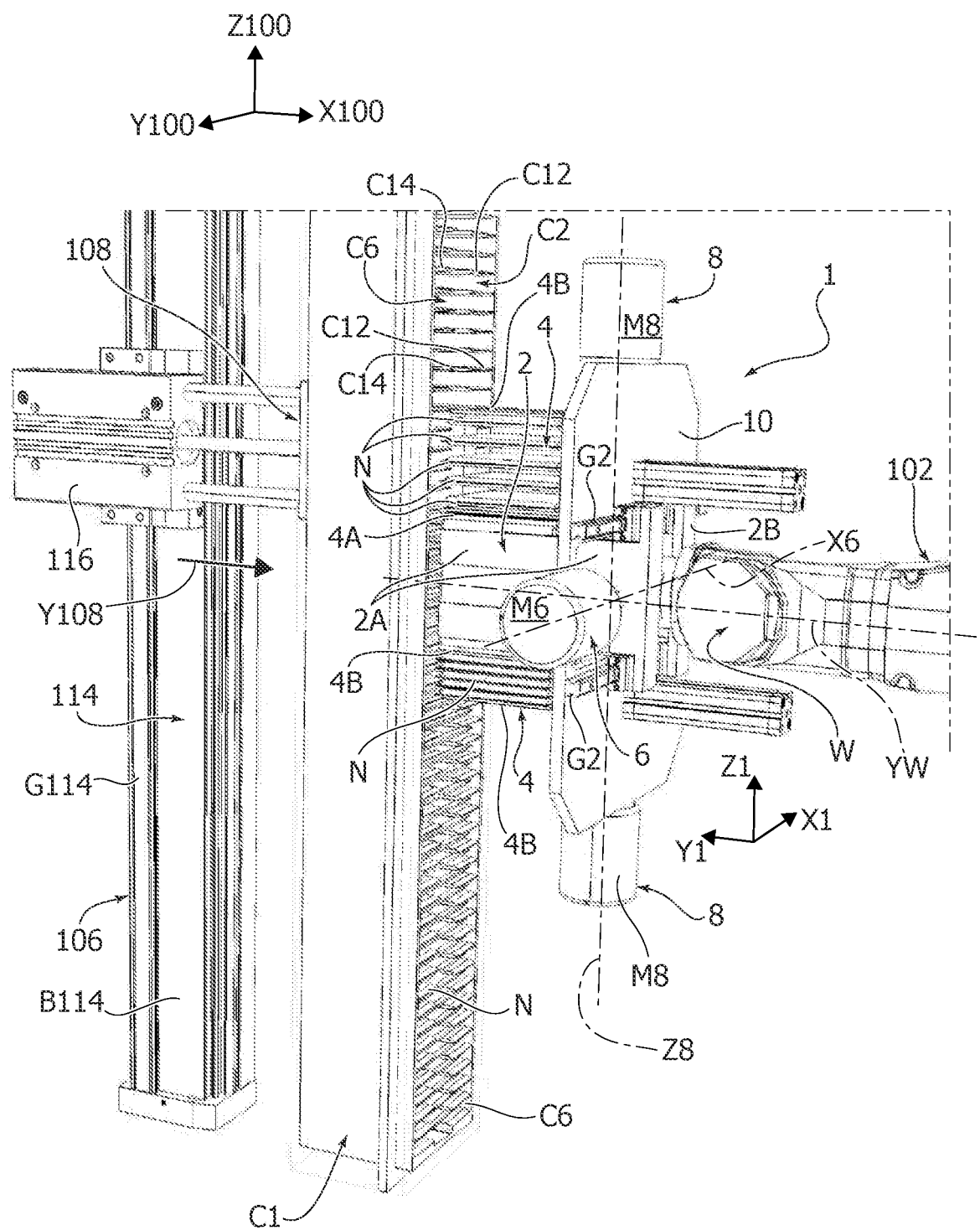
FIG. 2 is a perspective view according to pointer II in FIG. 1
Figure 3:
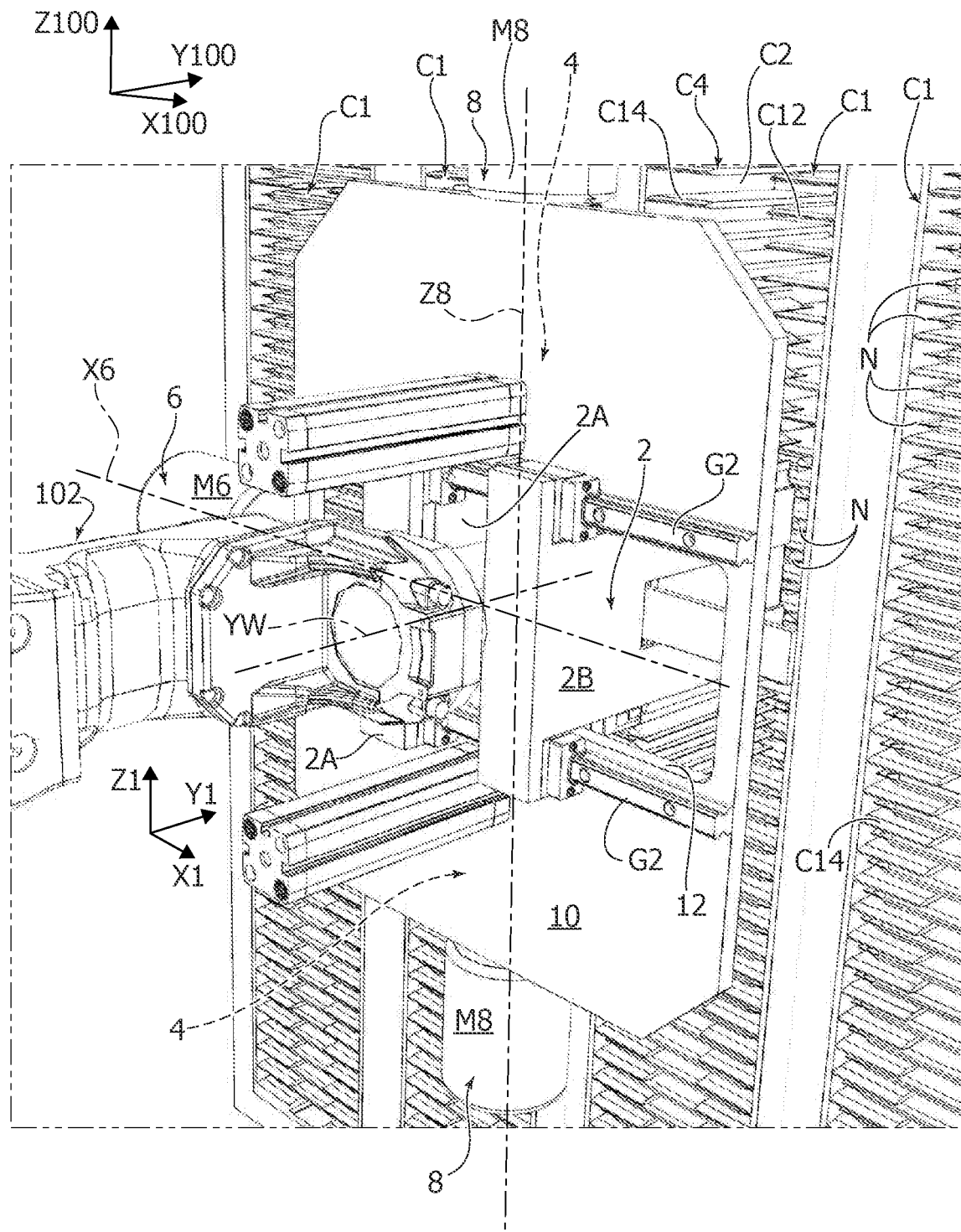
FIG. 3 is a perspective view according to pointer III in FIG. 1

Reference number 1 in FIGS. 1-4 and 6-9 designates as a whole a gripper for sanitary products N according to the invention. In most figures, the gripper 1 is shown in combination with an apparatus 100 for assembling kits of sanitary products according to the invention.

Throughout the description and the figures, two orthogonal reference systems will be used including:
 a first reference system X1-Y1-Z1 which is local to the gripper 1 and moves through space (translation and rotation) with the gripper 1
 a second reference system X100-Y100-Z100 which is local to the apparatus 100, and as such it is a fixed reference system.

In various embodiments, the gripper 1 is configured as an end effector for a manipulator such as a (multi axis) robot, and comprises:
 a first gripping section 2
 at least one second gripping section 4.

The first gripping section 2 comprises first and second gripping members 2A, 2B defining a first gripping span S2 therebetween, while each second gripping section 4 comprises third and fourth gripping members 4A, 4B defining a second gripping span S4 therebetween. Each gripping section 2, 4 is configured for gripping, handling and releasing respective batches of a kit of sanitary products N, such as sanitary napkins.

In a preferred embodiment such as that shown in the figures, the gripper comprises a first gripping section 2 and two second gripping sections 4 arranged on opposite sides of the first gripping section 2 and adjacent thereto, whereby the gripping members 2A, 2B are comprised between a pair of third gripping members 4A, while the gripping members 4B are in an outermost position. In general embodiments may be envisaged including one first gripping section and one second gripping section adjacent to one another, as well as embodiments including multiple first gripping sections and multiple second gripping sections arranged in an alternated fashion, whereby in general a first gripping section is adjacent to a second gripping section.

In the gripping section 2 the first gripping member 2A and the second gripping member 2B are operable to vary a mutual distance thereof along a first direction X6 parallel to direction X1, thereby varying the first gripping span S2 (which is also oriented parallel to direction X1).

In each of the second gripping sections 4, the third gripping member 4A and the fourth gripping member 4B are operable to vary a mutual distance thereof along a second direction Z8 parallel to the axis Y1, thereby varying the second gripping span S4 which is also oriented parallel to direction Y1. Accordingly, the first direction associated to the gripping span S2 and the second direction associated to the gripping span S4 are transverse to one another.

The first gripping section 2 comprises a first drive unit 6 configured to move the first gripping member 2A and the second gripping member 2B along the first direction X6, and wherein each second gripping section comprises a second drive unit configured to move the third gripping member 4A and the second gripping member 4B of each second gripping section 4 along the second direction Z8.

In preferred embodiments, the first drive unit 6 and each second drive unit 8 are independently operable. This means that the first gripping span S2 is adjustable independently of each second gripping span S4. Accordingly, a gripper 1 with three gripping sections 2, 4, 4 as shown in the figures features three independently adjustable gripping spans S2, S4, S4. However in alternative embodiments—while maintaining independency of adjustment of the gripping span S2 from the gripping span S4, it may be envisaged that the gripping members of the gripping sections 4 be dependently adjustable, i.e. the adjustment of the gripping span S4 of the two gripping sections 4 on opposite sides of the gripping section 2 be the same.

Operation of the gripping members 2A, 2B and 4A, 4B may in general depend on the arrangement of the gripper 1. In the embodiments shown herein, FIG. 4, the gripping members 2A, 2B are operable in a reciprocating fashion, i.e. they can be drawn near to one another or moved away from one another so that the gripping span S2 has a bilateral variation in any case (i.e. both at the gripping member 2A and at the gripping member 2B).

The gripping members 4A and 4B may be operated by the drive unit(s) identically to the members 2A, 2B are operated by the unit 6: operable in a reciprocating fashion, i.e. they can be drawn near to one another or moved away from one another so that the gripping span S4 has a bilateral variation in any case (i.e. both at the gripping member 4A and at the gripping member 4B).

As each kit of sanitary products comprising the batches gripped by the gripping sections 2, 4 is meant to be loaded altogether into a package, it is preferable to arrange the gripping sections to be as aggregate as possible to avoid wasting packaging space. Despite the bilateral movement of the gripping members, the excursions thereof are relatively small owing to the fact that the product N in the kit are actually shared among multiple gripping sections, whereby each gripping section 2, 4 has to deal with a smaller number of products, hence requires to establishing a smaller interference with the products N to grip them as compared to the handling of the entire kit by a single pair of gripping members.

The gripping members 4A, 4B may, however, be operated differently, for instance on account of the position thereof with respect to the gripping section 2. Each gripping member 4A is arranged essentially as a side member to the gripping members 2A, 2B that extends across the gripping span S2.

Figure 4:
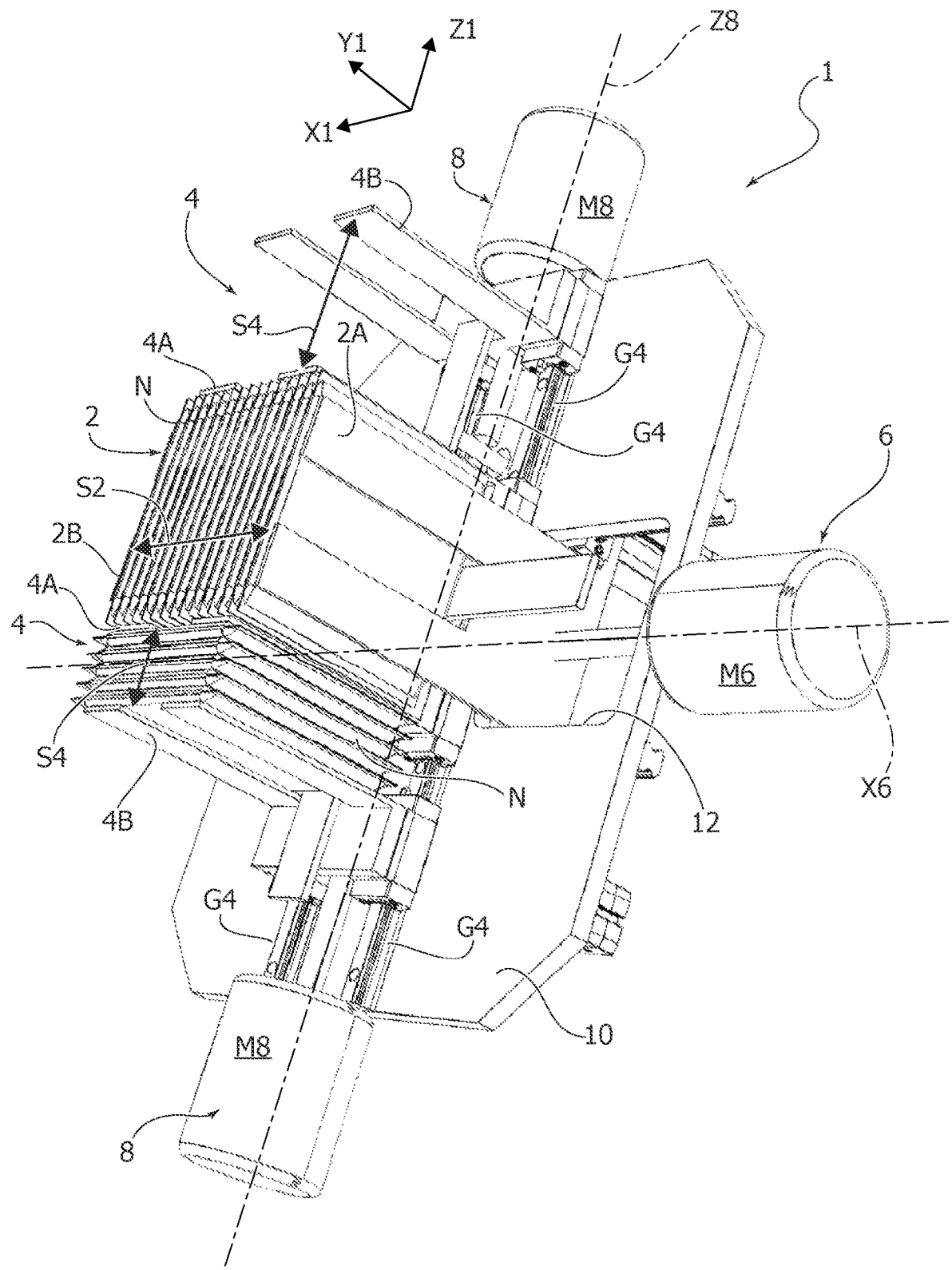
FIG. 4 is a perspective, isolated, view of the gripper according to the invention.

Under these circumstances, the drive unit 8 of each gripping section 4 is configured to operate the gripping members 4B only along the direction Z8, whereby the variation of the gripping span(s) S4 is achieved by drawing the member 4B near to the member 4A or moving the member 4B away from the member 4A. the member 4A may feature an independent adjustment mechanism that is configured to vary the position thereof with respect to the gripping members 2A, 2B, to accommodate larger (in the direction transverse to the span S2) sizes of sanitary products N between gripping members 2A, 2B than those shown in the figures (again, see FIG. 4 for reference).

The drive units 6, 8 may include various type of drivers, for instance—in the embodiment shown in the figures—an electric motor M6 (unit 6), M8 (unit 8) coupled to a screw drive that operates the gripping members 2A, 2B and 4B (where applicable, otherwise 4A and 4B) along directions Z6, Z8 respectively. Regardless of the specific type of driving unit, gripping members 2A, 2B and 4A, 4B are slidingly mounted on guides G2 (pairwise arranged, members 2A, 2B) and G4 (pairwise arranged, members 4A, 4B, and transverse to the guides G2). in some embodiments, each driving unit 6, 8 may include a linear motor whereby guides G2 and G4 may function as a stator of the linear electric motor, and each gripping member 2A, 2B and 4A, 4B may function as the cursor of the linear electric motor.

With reference again to FIG. 4, in preferred embodiments as shown herein the drive units 6, 8 as well as the gripping members 2A, 2B and 4A, 4B are mounted on a base plate 10, for instance with the guides G2, G4 on one side of the plate 6 and the gripping members 2A, 2B and 4A, 4B protruding to the opposite side of the plate 10 through a window 12 of the plate 10. The drive units 6, 8 may be indifferently fastened to either side of the plate 6.

With reference to FIGS. 1, 6, 7, 8, the apparatus 100 according to the invention will now be described, also adding further details as to the operation of the gripper 1.

The apparatus 100 includes a manipulator unit 102 including the gripper 1 as an end effector. In other terms, in preferred embodiments the manipulator unit 102 may include a robot (e.g. a multi-axis robot) having a wrist W to which the gripper 1 is attached. In a preferred embodiment as shown in the figures, the manipulator unit 102 is an overhead robot.

In a manner per se known, the gripper 1 is connected to the wrist W so that it is movable in space (X100-Y100-Z100) as determined by the robot/manipulator unit 102, and to be rotatable around axes parallel to X1, Z1, and also rotatable around an axis YW orthogonal to the above two axes.

The apparatus 100 includes at least one storage unit 104 for sanitary products, the storage unit 104 comprising an array of containers C1, preferably of the type disclosed in European Patent Application no. 21201297.5. For the purposes of recalling fundamental features of such container, with reference to FIGS. 1A and 1B, each container C1 is a rack container comprising a rack of slot-like housings C2, each of said slot-like housings C2 being configured to accommodate a sanitary product N (for instance a sanitary napkin N) and being separated by a baffle C4.

Each of the housings C2 has an inlet opening C6, with all of the inlet openings C6 facing on one and the same side of the container Cl. The housings C2 are fully independent from each other, i.e. each of the housing C6 is configured to allow loading of a sanitary product, particularly a sanitary napkin N, therein and withdrawal of the sanitary product therefrom independently of the other housings 2.

In the preferred embodiment shown in the figures, the container 1 has a container body C8 essentially prismatic (parallelepiped) in shape which is open to the outside where all of the inlet openings C6 give out, and which includes a cutaway C10 which extends across the rack of housings C2 and is arranged on an opposite side with respect to the inlet openings. Accordingly, each housing C2 comprises a first open end at the inlet opening C6, and a second open end at the cutaway C10, the second open end being opposite to the first open end. In other words, the cutaway C10 makes the housings C2 through housings, even though introduction and extraction of sanitary napkins N from the housings C2 is only allowed through the inlet openings C6.
1.
Owing to the cutaway, each baffle C4 includes a first portion C12 and a second portion C14 arranged on opposite sides of the cutaway C10. Preferably, each baffle lies recesses with respect to the edge of the cutaway C10, i.e. it does not extend to the edge of the cutaway C10. In this regard, further cutaways C16, C18 may be advantageously provided at each pair of baffle portions C12, C14 respectively, so that the walls of the container body C8 arranged on opposite sides of the cutaway C10 have an overall comb-like shape due to the provision of the cutaways C16 and C18.

In preferred embodiments, each container C1 is loaded into a supporting shelf or rack allowing for an ordinate arrangement of the containers C1, for instance as a linear array oriented along direction X100. preferably, storage units 104 are arranged on opposite sides of the manipulator 102, so that a double (or a higher, in general) number of sanitary products N to be handled may be arranged at the manipulator 2.

The apparatus 100 also includes an extractor unit 106 arranged on the cutaway side of the containers C1, i.e. on an opposite side to that the manipulator unit 102 is presented with. An extractor unit 106 is provided for each storage unit 104.

The extractor unit 106 comprises an extractor 108 and a drive facility 110. The drive facility 110 is configured to move the extractor 108 across the array of containers C1 of the storage unit 104 and across the slot like housings C2 of each container Cl. In other terms, the extractor 108 is configured for "scanning" the array of containers by moving in the X100-Z100 plane thanks to the drive facility 110.

Figure 5:
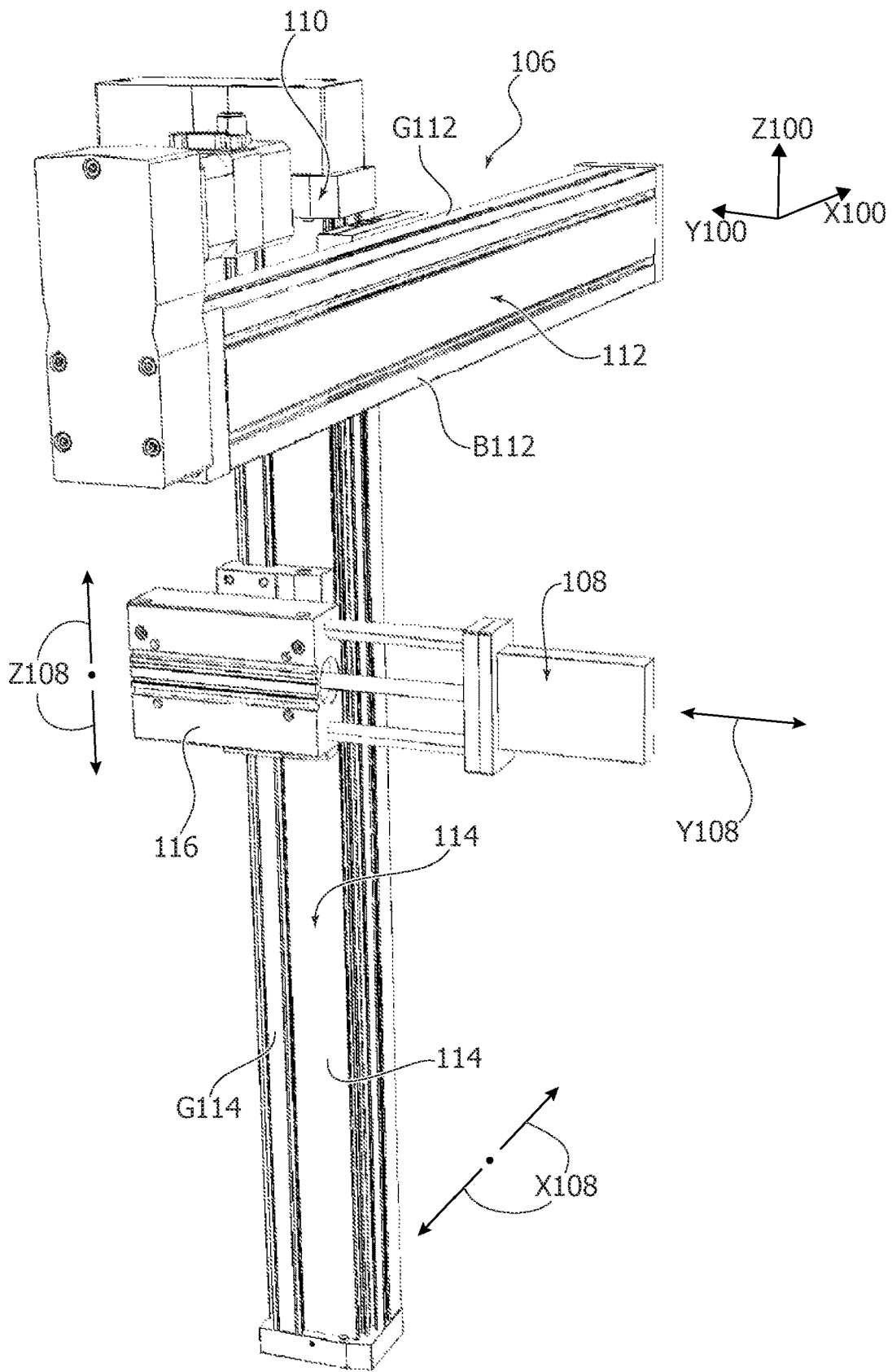
FIG. 5 is a perspective, isolated, view of a portion of the apparatus according to the invention.

In greater detail, with reference to FIG. 5, the drive facility 110 comprises a horizontal drive unit 112, a vertical drive unit 114, and an extractor drive unit 116. The vertical drive unit 114 is itself movable horizontally driven by the horizontal drive unit 112 and carries the extractor drive unit 116, which in turn is couped to the extractor 108, which is essentially a pusher member. Each drive unit 112, 114 comprises a supporting beam B112, B114 provided on which is a guide member G112, G114. The guide member G112 is engaged by a slider S112 through which the vertical drive unit 112 translates horizontally along the beam B114, operated by, for instance, a screw drive (electric motor and screw engaged by the slider), or a linear motor drive (guide G114 may provide the stator, slider S112 the cursor/slider of the linear motor).

The guide member G112 is engaged by the extractor drive unit 116 which is itself configured as a slider (and can be operated, accordingly, ad disclosed above in respect of slider member S112) and is configured for driving a back and forth motion Y108 of the extractor 108. With guide member G114 allowing a horizontal motion X108 (again, back and forth) of the drive unit 112 with the extractor 108 attached (hence of the extractor 108 itself), and guide member G112 allowing a vertical motion Z108 (up and down) of the extractor 108, the extractor 108 is actually movable along the three main spatial directions X100, Y100, Z100 so that it is able to scan the array of containers C1 while at the same time being able to move back and forth with respect to the scanning plane.

The extractor 108 is accordingly operable (motion Y108) to enter a container C1 through the cutaway C10 thereof to extract one or more sanitary products N from the respective slot like housings C2, wherein each set of sanitary products N extracted from the container C1 corresponds to a batch of a kit of sanitary products to be assembled into a kit and packaged.

To this end, the apparatus 100 includes a conveying unit 118 configured for carrying a plurality of packages K for sanitary products N along a conveying direction parallel to direction X100. Each package K is configured as a box package intended to accommodate a kit of different sanitary products N, for instance different sanitary napkins for different blood flow regimes through the period.

Operation of the apparatus 100 and the gripper 1 attached thereto will now be described.

Through the apparatus 100 and the gripper 102 groups of sanitary products N from different containers C1 or from the same container C1 (depending on how the container(s) were loaded prior to being transferred to the storage units 104) can be loaded onto the gripper 1, and transferred to a package K already pre-assembled into a kit. Pre-assembly occurs on the gripper 1: the provision of multiple gripping sections serves to allow the individual loading of different groups of sanitary products N in a respective gripping section, whereby when all of the gripping sections 2, 4 are loaded, the kit is actually assembled at the very gripping sections.

In greater detail, the manipulator 102 is configured to position the gripper 1 at a rack container C1 on an opposite side of the extractor unit 106 to receive one or more sanitary products N from the rack container C1 concerned following extraction thereof by the extractor 108.

The container C1 to be subject to an extraction operation is determined based on the type of product loaded therein. For exemplary (and in no way limiting) purposes, it will be assumed that the kit to be loaded into a package K comprises a first number of sanitary products N of a first type, a second number of sanitary products N of a second type, and a third number of sanitary products N of a third type. The kit of sanitary products N to be loaded in the package K thus comprises the first number of sanitary products as first batch of the kit, the second number of sanitary products as second batch of the kit, and the third number of sanitary products as third batch of the kit. The first batch is to be loaded into the first gripping section, the second batch is to be loaded into the second gripping section, and the third batch is to be loaded into the third gripping section.

The first, second and third numbers may in principle be different from each other, or identical, or partly identical (i.e. two identical, one different) depending on the needs. Each product is a sanitary napkin, which has a flat shape matching that of the slot like housings C1.

Again for exemplary purposes, as this generally depends on how the containers C1 are loaded, it will be assumed that the three types of products N concerned are located in three distinct containers C1.

The extractor unit 106 on the side of the manipulator 102 (or—equivalently in these embodiments—on the side of the conveying unit 118) at which the container C1 holding the products N of the first batch of the kit is located is activated so that the extractor 108 is positioned at the cutaway of the container C1 in a position that overlaps a number of slot-like housings C2 corresponding to the first number of products N. it should be noted that, where the number of products N span a larger distance than the relevant dimension of the extractor 108 along the cutaway 10, the drive unit 114 will be operated to intercept all of the required products N in two (or more) stages.

The manipulator 102, on its hand, is configured for positioning the gripper 1 so to present the gripping section 2 with the products to be loaded therein, which are still lying in the housings C2. The gripping span S2 may be preliminarily adjusted to adapt to the size of the group of products to be loaded into the gripping section 2. in this regard, each of the first and second gripping sections 2, 4 of the gripper 1 is operable between a reception position and a gripping position, wherein in the reception position the respective gripping span S2, S4 is controlled to a value greater than the dimension of the batch of the kit of sanitary product N to be loaded into the gripping section in the direction of the gripping span S2, S4. This facilitates insertion of the products N into the gripping section 2, 4, as it avoids any interference with the products N.

Conversely, in the gripping position the respective gripping span S2, S4 is controlled to a value smaller than the dimension of the batch of the kit of sanitary products in the direction of the gripping span S2, S4 (hence smaller than in the reception position). This allows moving the products through the space as it sets up an interference condition which keeps the products N onto the gripper 1.

When the gripping section 2 is standing by—already in the reception position—in front of the products N of the first batch of the kit (FIGS. 6, 7—which, although relating to the loading of section 4 are readily applicable to the loading of section 2 for obvious reasons), the extractor 108 is advanced through the cutaway 10 (Y108) and the products N are transferred to the first gripping section 2. The gripping members 2A, 2B are operated to the gripping position and another loading cycle can begin. In this regard, Since the gripping sections 2, 4 have gripping spans extending along transverse directions, and accordingly have gripping members 2A, 2B and 4A, 4B capable of supporting sanitary products N against gravity only when they are arranged horizontally, it follows that in the transition from the loading of the first gripping section 2 to the loading of the second gripping section(s) 4 the manipulator 2 will have to rotate the gripper 1 90 degrees around the axis YW to present the gripping members 4A, 4B with a horizontal orientation, as keeping the gripping members 2A, 2B horizontal at the gripping section 2 in the previous loading cycle necessarily implies that the gripping members 4A, 4B were vertical. In general, the manipulator 102 is configured for rotating the gripper 1 around the axis YW so that the first gripping span S2 or the second gripping span S4 are oriented with the respective first direction X6 or second direction Z8 along the rack of slot like housings C2.

Figure 6:
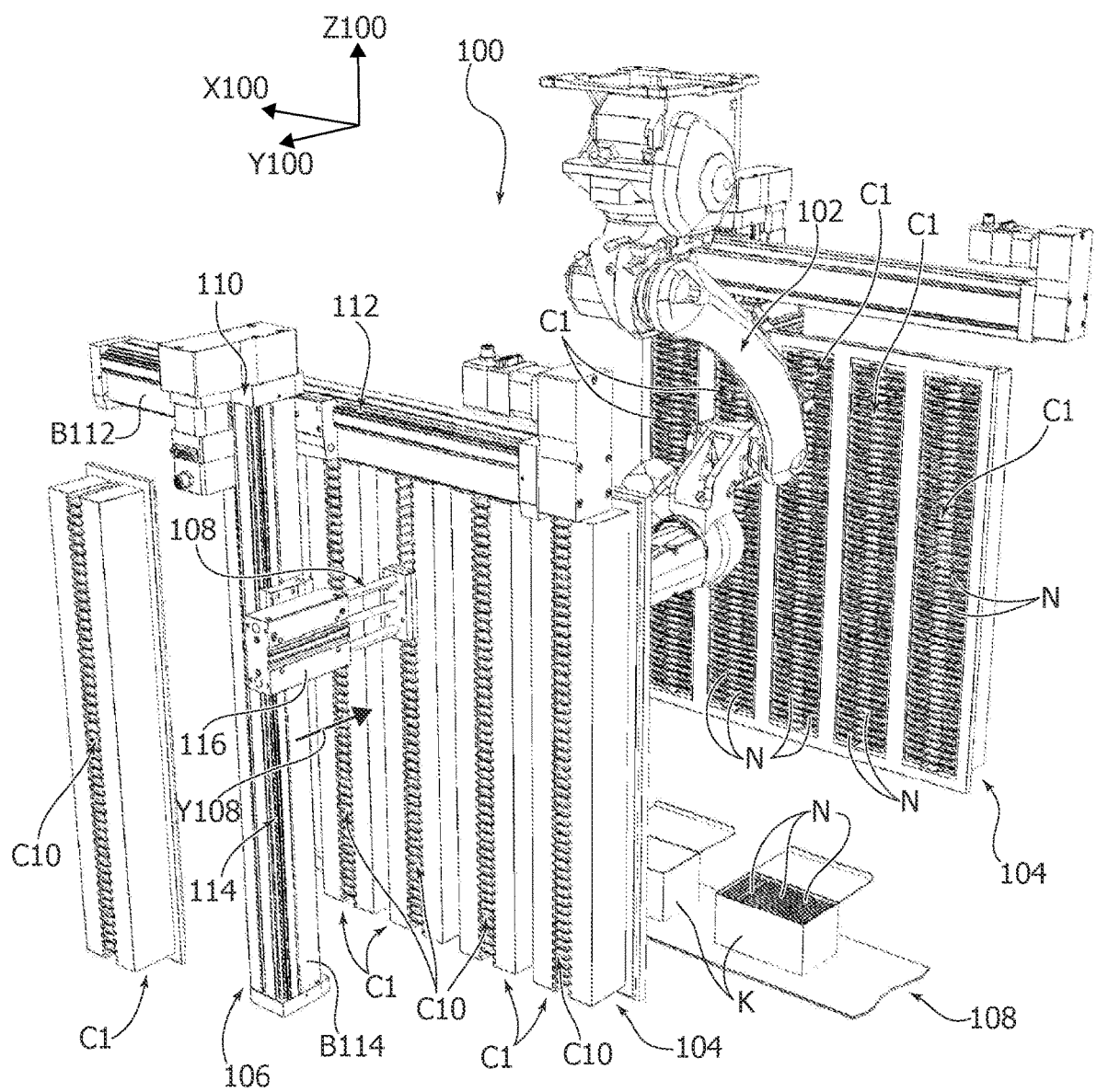
FIGS. 6 and 7 are a perspective, and a close-up perspective views of the apparatus of the invention in a first operating condition, and with some components removed to expose other components or functional interactions otherwise not visible.
Figure 7:
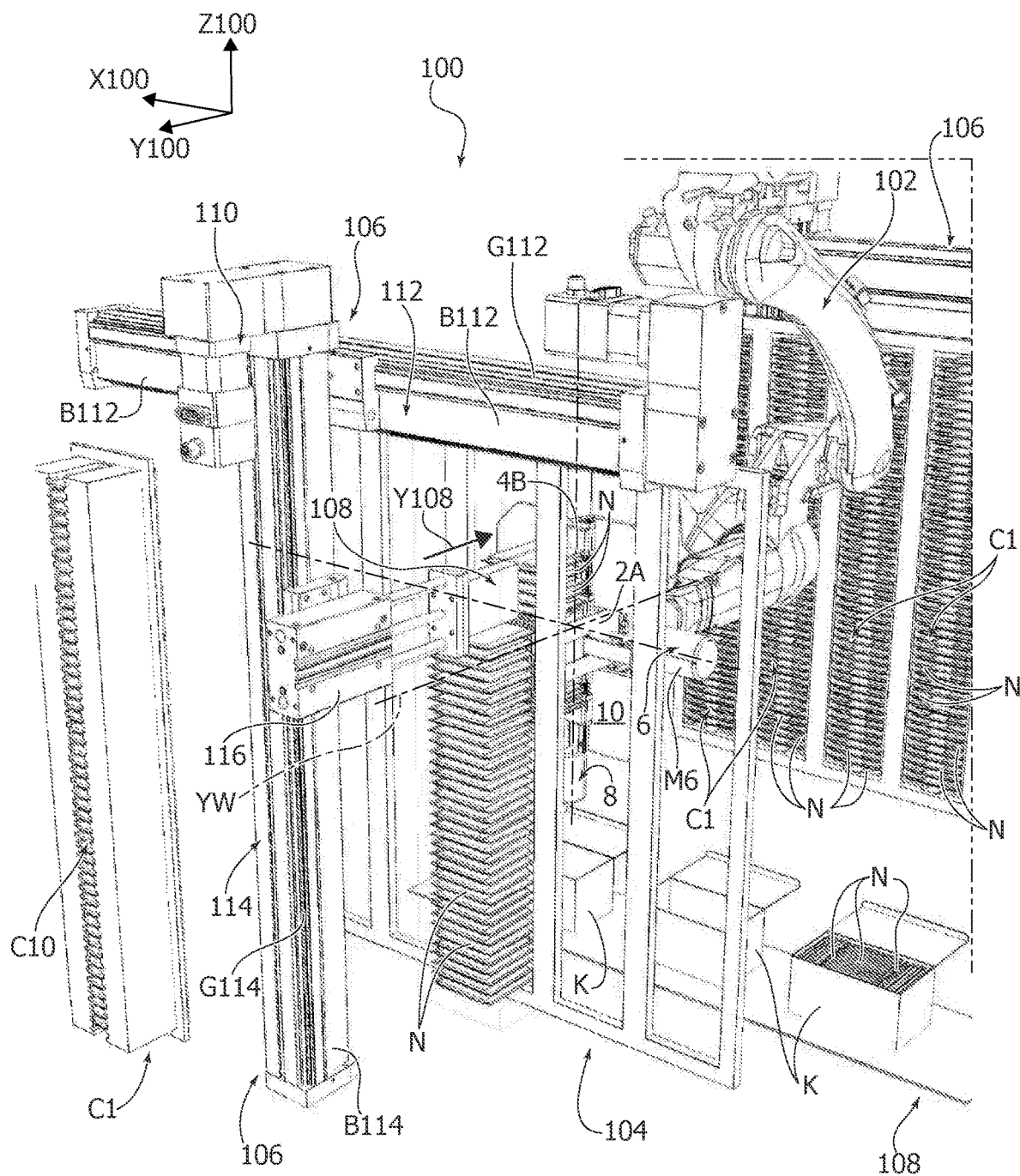

The loading cycle for the second batch of the kit of products N unfolds exactly as disclosed in respect of the first batch: the extractor 108 is positioned at the products to be loaded, whereby if the container C1 is on the same side of the manipulator 102 as the container C1 which provided the first batch of the kit the same extractor unit 106 will have to be operated again to scan the array of containers to the target location, otherwise the extractor unit 106 on the opposite side will have to be activated and operated just as described: scanning of the array of containers C1 to the target location and operation of the extractor 108 to load the second batch of the kit of products into the gripping section 4 (again, see in particular FIGS. 6, 7). The gripping members 4A, 4B are accordingly moved from the reception position to the gripping position.

The last batch of the kit of products N is loaded onto the remaining gripping section 4 just as disclosed above in respect of the second batch, only in this case there may be no need for a further rotation of the gripper 1 to present the gripping members 4A, 4B with a horizontal orientation. A rotation around the axis YW may nevertheless be necessary in cases where it results in a better positioning of the gripping section 4 to be loaded, for instance based on the position of the container providing the third batch of the kit of products N.

Loading being complete, and all of the gripping sections 2, 4 being with gripping members 2A, 2B, and 4A, 4B in the gripping position, the manipulator 102 is ready to transfer the gripper 1 to the conveying unit 118 to release the kit of products N into a package K. In this regard, it is noted that the gripper 1 is inherently universal as far as the kit to be assembled is concerned: provided that the gripping members 2A, 2B and 4A, 4B do not exceed the relevant inner dimensions of the package K, the batches of sanitary products assembled into a kit will always match the inner dimensions of the package K which is deigned for the kit itself.

Figure 8:
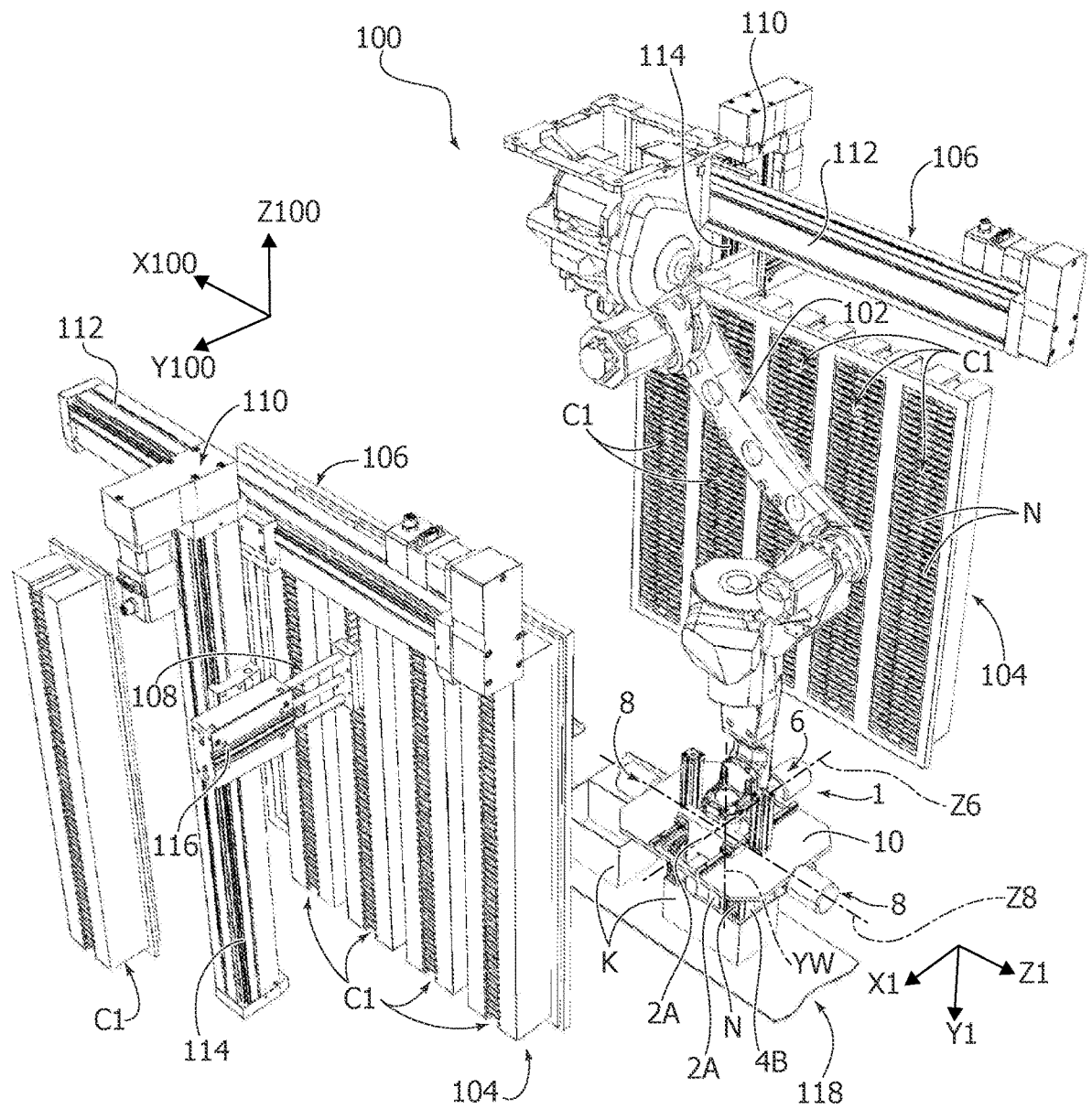
FIGS. 8 and 9 are a perspective, and a close-up perspective views of the apparatus of the invention in a second operating condition, and—again—with some components removed to expose other components or functional interactions otherwise not visible.
Figure 9:
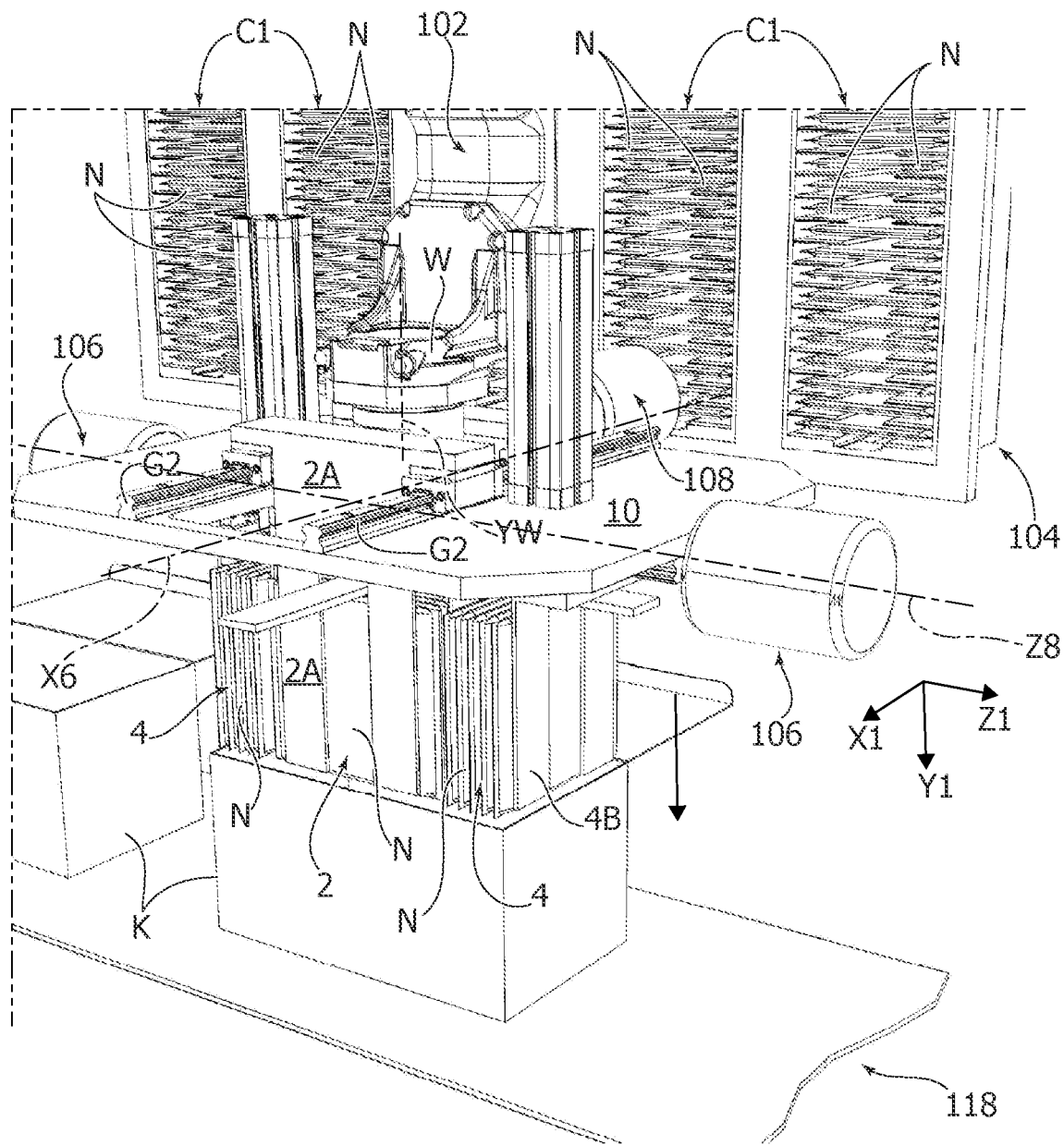

FIGS. 8 and 9 show the insertion of the kit of products N into the package K: the gripper 1 is positioned overhead to the package K with the gripping sections 2, 4 facing the inner volume of the package. The gripper is therefore advanced towards the package (vertically) to position the gripping members 2A, 2B and 4A, 4B into the package K: this already places the kit into the package. Release is accomplished by increasing the gripping spans S2, S4 to the point where interference with the batches of products in each griping section is lost: this immediately releases the products N from the gripping sections 2, 4 by gravity.

This is where a technical advantage of the configuration of the gripper 1 according to the invention comes into play: unlike prior art grippers, which only feature a single gripping section which sets up or releases interference along a single direction, the gripper 1 is capable of a multi-directional gripping-and-release action, as the (variable) gripping spans are transverse to each other. With a prior art gripper, releasing the interference to release the product may oftentimes lead to rupture of the package K or jamming of the gripper inside the package: the excursion of the gripping members generally requires a play within the package that logistics simply won't allow, as it would amount to make a package bigger than needed only to accommodate the excursion of a gripper, thereby resulting in a certain amount of package volume being wasted for purely functional reasons and not used for storage purposes.

Conversely, with the multi directional gripping-and-release action the gripper 1 is capable of, the excursions of the gripping members 2A, 2B and 4A, 4B are first of all comparatively smaller than the prior art due to the lower number of products N each gripping section has to deal with, then the gripping section(s) 4 may take advantage of an extra play for releasing the products N by slightly intruding the area between the gripping members 2A, 2B (the bilateral/reciprocating motion of gripping members 4A, 4B allows this). Note that even when the movement of the gripping members 4A, 4B is not bilateral, the reduced excursion of the gripping members 4A, 4B does not result in jamming of the gripper of rupturing or tearing of the package K.

This results ultimately in a safe and effective release of the kit of products N into the package K. the gripper 1 is then retracted from the package K and new loading cycles can begin. This overall affords higher operational rates as the interaction with the packages K is inherently smoother, and also allows greater efficiency in that less (virtually none) packages are discarded for quality reasons.

Accordingly, and by way of summary, a method of assembling kits of sanitary products by means of the apparatus 100 is also within the scope of the invention, wherein the method comprises:

positioning the gripper 1 at a rack container C1 on the side of the inlet openings C6 thereof with one of the first gripping section 2 and the at least one second gripping section 4 in the reception position and with the respective first gripping span S2 or second gripping span S4 extending over a number of inlet openings C6 corresponding to a first batch of a kit of sanitary products N to be loaded onto the one of the first gripping section 2 and the at least one second gripping section 4, positioning the extractor 108 of the extractor unit 106 on the side of the cutaway C10 of the rack containers C1, and advancing the extractor through the cutaway C10 of the rack container C1 to extract the first batch of the kit of sanitary products N to be loaded onto the one of the first gripping section 2 and the at least one second gripping section 4, controlling the gripping span S2 or S4 of the one of said first gripping section S2 and the at least one second gripping section S4 to achieve the gripping position, positioning the gripper 1 at a rack container C1 on the side of the inlet openings C6 thereof with the other of the first gripping section 2 and the at least one second gripping section 4 in the reception position and with the respective first gripping span S2 or second gripping span S4 extending over a number of inlet openings C6 corresponding to at least one second batch of a kit of sanitary products N to be loaded onto the other of the first gripping section 2 and the at least one second gripping section 4, positioning the extractor 108 of the extractor unit 106 on the side of the cutaway C10 of the rack container Cl, and advancing the extractor 108 through the cutaway C10 to extract the at least one second batch of the kit of sanitary products N to be loaded onto the other of the first gripping section 2 and the at least one second gripping section 4, controlling the first gripping span S2 or the second gripping span S4 of the other of said first gripping section 2 and the at least one second gripping section 4 to achieve the gripping position, positioning the gripper 1 comprising the kit of sanitary products N loaded into the first gripping section 2 and the at least one second gripping section 4 at a package (K) for sanitary products, and introducing the kit of sanitary products (N) into the package (K), increasing the gripping span S2, S4 of the one and of the other of said first gripping section 2 and the at least one second gripping section 4 to release the kit of sanitary products into the package K.

According to embodiments of the invention, and depending on how the containers C1 are loaded, positioning the gripper 1 at a rack container C1 on the side of the inlet openings thereof with one of the first gripping section 2 and the at least one second gripping section 4 in the reception position and said positioning the gripper 1 at a rack container on the side of the inlet openings C6 thereof with the other of the first gripping section 2 and the at least one second gripping section 4 in the reception position comprises positioning the gripper 1 at different rack containers C1.

According to embodiments of the invention positioning the gripper 1 at a rack container C1 on the side of the inlet openings C6 thereof with one of the first gripping section 2 and the at least one second gripping section 4 in the reception position and said positioning the gripper 1 at a rack container on the side of the inlet openings C6 thereof with the other of the first gripping section 2 and the at least one second gripping section 4 in the reception position comprises positioning the gripper 1 at different sets of inlet openings C6 of the same rack container Cl, for instance when a rack container C1 is loaded with multiple types of sanitary products N to be assembled in a kit.

Naturally, while the principle of the invention remains the same, the details of construction and the embodiments may widely vary with respect to what has been described and illustrated purely by way of example, without departing from the scope of the present invention.

The invention claimed is:

1. An apparatus for assembling kits of sanitary products, comprising:
   a manipulator unit including a gripper as an end effector,
   at least one storage unit for the sanitary products, the storage unit comprising an array of containers, each of the containers being a rack container comprising a rack of slot-like housings, each of said slot-like housings being configured to accommodate a sanitary product and being separated by a baffle, wherein each of the slot-like housings has an inlet opening, all of the inlet openings facing on one and the same side of the container, and further wherein said each baffle includes a first portion and a second portion arranged on opposite sides of a cutaway, the cutaway extending across the rack of slot-like housings and being arranged on an opposite side to the inlet openings,
   an extractor unit comprising an extractor and an extractor drive facility configured to move the extractor across the array of containers of the storage unit and across the slot-like housings of each container, the extractor being operable to enter each container through the cutaway thereof to extract a batch of sanitary products from the respective slot-like housing, and a conveying unit configured for carrying a plurality of packages for sanitary products,
wherein the gripper comprises:
a first gripping section,
at least one second gripping section,
the first gripping section comprising first and second gripping members defining a first gripping span therebetween,
each second gripping section comprising third and fourth gripping members defining a second gripping span therebetween,
wherein the first gripping member and the second gripping member are operable to vary a mutual distance thereof along a first direction, thereby varying the first gripping span therebetween,
wherein the third gripping member and the fourth gripping member of each second gripping section are operable to vary a mutual distance thereof along a second direction, thereby varying the second gripping span therebetween,
the first direction being transverse to the second direction,
wherein each of the first and second gripping sections is operable between a reception position and a gripping position, wherein in the reception position the respective gripping span is controlled to a value greater than the respective gripping span in the gripping position,
wherein the manipulator unit is configured to position the gripper at a rack container on an opposite side of the extractor unit to receive the batch of sanitary products from the rack container following extraction thereof by the extractor, each batch of sanitary products being received at one of said first gripping section and second gripping sections, and
wherein the manipulator unit is configured for positioning the gripper with batches of sanitary products in the first and second gripping sections at a package on said conveying unit to load the batches of sanitary products into the package.

2. The apparatus of claim 1, wherein the extractor unit is configured to extract batches of different sanitary products from the containers in the storage unit and loading each batch of sanitary products into a corresponding one of the first gripping section and the at least one second gripping section.

3. The apparatus of claim 1, wherein in the reception position of each of the first and second gripping sections, the first gripping span associated with the first gripping section and the second gripping span of the second gripping sections are controlled to a value greater than a dimension of the batch of sanitary products in the direction of the first and second gripping spans, and
wherein in the gripping position of each of the first and second gripping sections, the respective first and second gripping spans are controlled to a value smaller than the dimension of the batch of sanitary products in the respective first and second directions of the first and second gripping spans.

4. The apparatus of claim 1, comprising a plurality of storage units on opposite sides of the conveying unit, and wherein the manipulator unit is arranged amid the storage units on opposite sides of the conveying unit.

5. The apparatus of claim 1, wherein the first gripping section is adjacent to each of the at least one second gripping section.

6. The apparatus of claim 1, wherein the first gripping section comprises a first drive unit configured to move the first gripping member and the second gripping member along the first direction, and wherein each of the at least one second gripping section comprises a second drive unit configured to move the third gripping member and the second gripping member along the second direction.

7. The apparatus of claim 6, wherein the first drive unit and said each second drive unit are independently operable.

8. The apparatus of claim 7, wherein the first gripping span is adjustable independently of said each second gripping span.

9. The apparatus of claim 6, wherein the first drive unit is configured to operate the first gripping member and the second gripping member, and the second drive unit is configured to operate the third gripping member and the fourth gripping member in a reciprocating fashion to vary the first and second gripping spans thereof.

10. The apparatus of claim 1, wherein the at least one second gripping section comprises two second gripping sections arranged on opposite sides of the first gripping section and adjacent thereto.

11. A method of assembling kits of sanitary products by means of an apparatus according to claim 1, the method comprising:
positioning the gripper at the rack container on the side of the inlet openings thereof with one of the first gripping section and the at least one second gripping section in the reception position and with the respective first gripping span or second gripping span extending over a number of inlet openings) corresponding to a first batch of a kit of sanitary products to be loaded onto the one of the first gripping section and the at least one second gripping section,
positioning the extractor of the extractor unit on the side of the cutaway of the rack containers, and advancing the extractor through the cutaway of the rack container to extract the first batch of the kit of sanitary products to be loaded onto the one of the first gripping section and the at least one second gripping section,
controlling the gripping span of the one of said first gripping section and the at least one second gripping section to achieve the gripping position,
positioning the gripper at the rack container on the side of the inlet openings thereof with the other of the first gripping section and the at least one second gripping section in the reception position and with the respective first gripping span or second gripping span extending over a number of inlet openings corresponding to at least one second batch of the kit of sanitary products to be loaded onto the other of the first gripping section and the at least one second gripping section,
positioning the extractor of the extractor unit on the side of the cutaway of the rack container, and advancing the extractor through the cutaway to extract the at least one second batch of the kit of sanitary products to be loaded onto the other of the first gripping section and the at least one second gripping section,
controlling the first gripping span or the second gripping span of the other of said first gripping section and the at least one second gripping section to achieve the gripping position,
positioning the gripper comprising the kit of sanitary products loaded into the first gripping section and the at least one second gripping section at the package for sanitary products, and introducing the kit of sanitary products into the package, increasing the gripping span of the one and of the other of said first gripping section and the at least one second gripping section to release the kit of sanitary products into the package.

12. The method of claim 11, wherein said positioning the gripper at the rack container on the side of the inlet openings thereof with one of the first gripping section and the at least one second gripping section in the reception position and said positioning the gripper at the rack container on the side of the inlet openings thereof with the other of the first gripping section and the at least one second gripping section in the reception position comprises positioning the gripper at different rack containers.

13. The method of claim 12, wherein said positioning the gripper at the rack container on the side of the inlet openings thereof with one of the first gripping section and the at least one second gripping section in the reception position and said positioning the gripper at the rack container on the side of the inlet openings thereof with the other of the first gripping section and the at least one second gripping section in the reception position comprises positioning the gripper at different sets of inlet openings of the same rack container.

\* \* \* \* \*

UNITED STATES PATENT AND TRADEMARK OFFICE
CERTIFICATE OF CORRECTION

| | |
|---|---|
| PATENT NO. | : 12,030,682 B2 |
| APPLICATION NO. | : 18/080800 |
| DATED | : July 9, 2024 |
| INVENTOR(S) | : Gabriele Sablone |

It is certified that error appears in the above-identified patent and that said Letters Patent is hereby corrected as shown below:

On the Title Page

Item (71) Applicant address information should be listed as:
- Fameccanica.Data S.p.A., San Giovanni Teatino (Chieti), ITALY -

Item (72) Inventor address information should be listed as:
- Gabriele SABLONE, San Giovanni Teatino (Chieti), ITALY -

Signed and Sealed this
Seventeenth Day of June, 2025

Coke Morgan Stewart
*Acting Director of the United States Patent and Trademark Office*